(12) United States Patent
Monzani et al.

(10) Patent No.: US 9,944,593 B2
(45) Date of Patent: Apr. 17, 2018

(54) PROCESS FOR THE SYNTHESIS OF FLUORALKYL SULFONATE SALTS

(71) Applicant: SOLVAY SPECIALTY POLYMERS ITALY S.P.A., Bollate (IT)

(72) Inventors: Cristiano Monzani, Trezzo Sull'adda (IT); Vito Tortelli, Milan (IT)

(73) Assignee: SOLVAY SPECIALTY POLYMERS ITALY S.P.A., Bollate (MI) (IT)

( * ) Notice: Subject to any disclaimer, the term of this patent is extended or adjusted under 35 U.S.C. 154(b) by 0 days.

(21) Appl. No.: 15/027,167

(22) PCT Filed: Sep. 30, 2014

(86) PCT No.: PCT/EP2014/070952
§ 371 (c)(1),
(2) Date: Apr. 4, 2016

(87) PCT Pub. No.: WO2015/049239
PCT Pub. Date: Apr. 9, 2015

(65) Prior Publication Data
US 2016/0237028 A1    Aug. 18, 2016

(30) Foreign Application Priority Data

Oct. 4, 2013 (EP) .................................. 13187325

(51) Int. Cl.
| | | |
|---|---|---|
| C07C 303/32 | (2006.01) | |
| C07D 213/20 | (2006.01) | |
| C07C 277/08 | (2006.01) | |
| C07C 209/00 | (2006.01) | |
| C07D 487/04 | (2006.01) | |
| C07C 211/63 | (2006.01) | |
| C07C 279/06 | (2006.01) | |
| C07C 309/06 | (2006.01) | |

(52) U.S. Cl.
CPC .......... *C07C 303/32* (2013.01); *C07C 209/00* (2013.01); *C07C 211/63* (2013.01); *C07C 277/08* (2013.01); *C07C 279/06* (2013.01); *C07C 309/06* (2013.01); *C07D 213/20* (2013.01); *C07D 487/04* (2013.01)

(58) Field of Classification Search
CPC ........................... C07C 303/32; C07D 213/20
See application file for complete search history.

(56) References Cited

U.S. PATENT DOCUMENTS

| 3,919,295 A | 11/1975 | Wechsberg et al. |
| 4,168,277 A | 9/1979 | Mitschke et al. |
| 5,488,147 A * | 1/1996 | Vogel .................. C07C 17/12 |
| | | 562/113 |
| 5,498,754 A * | 3/1996 | Nakamura ............ C07C 303/44 |
| | | 562/113 |
| 6,235,921 B1 * | 5/2001 | Kobayashi ............ C07C 303/34 |
| | | 558/47 |
| 6,743,947 B1 | 6/2004 | Xu et al. |
| 2007/0100184 A1 | 5/2007 | Harmer et al. |
| 2007/0131535 A1 | 6/2007 | Shiflett et al. |
| 2007/0135645 A1 | 6/2007 | Ignatyev et al. |
| 2007/0265453 A1 | 11/2007 | Welz-Biermann et al. |
| 2010/0187481 A1 | 7/2010 | Bodesheim et al. |
| 2010/0204521 A1 | 8/2010 | Harmer et al. |

FOREIGN PATENT DOCUMENTS

| DE | 1966931 A | 5/1975 |
| EP | 363094 A1 | 4/1990 |
| EP | 726249 A1 | 8/1996 |
| WO | 2012156540 A2 | 11/2012 |

OTHER PUBLICATIONS

Kulkarni Prashant S. et al;, "Comparison of physicochemical properties of new ionic liquids based on imidazolium, quaternary ammonium, and guanidinium cations", Chemistry—A European Journal, 2007, vol. 13(30), p. 8478-8488—Wiley-VCH Verlag GmbH&Co KGaA, Weinheim.
Kunkel Helene et al., "Hexaalkylguanidinium trifluoromethanesulfonates—a general synthesis from tetraalkylureas and triflic anhydride, and properties as ionic liquids", European Journal of Organic Chemistry, 2007, (22), p. 3746-3757—Wiley-VCH Verlag GmbH&Co KGaA, Weinheim.
Ignat'Ev Nikolai V. et al., "A convenient synthesis of triflate anion ionic liquids and their properties", Molecules, 2012, vol. 17, p. 5319-5338.
Burdon J. et al., "Trifluoromethane sulfonate esters and their alkylating properties", Tetrahedron, 1965, vol. 21, p. 1-4—Elsevier Science Publishers, Amsterdam, NL.
Takahashi Kohta et al., "Development of triarylamine mediator having ionic-tag and its application to electrocatalytic reaction in ionic liquid", Electrochimica Acta, 2012, vol. 77, p. 47-53—Elsevier Ltd.
Storzer W. et al., "Novel Routes to Fluorinated Ethers Containing a Fluorosulfonyl Group", Journal of Fluorine Chemistry, Jul. 1, 1992 , vol. 58, No. 1, p. 59-69—Elsevier Sequoia.
Chin Chong Shik et al., "Activation of Acetonitrile in [Cp*Ir(η3-CH2CHCHPh)(NCMe)]+: Crystal Structures of Iridium-Amidine, Imino-Ether, Amido, and Amide Complexes", Organometallics, 2000, vol. 19(4), p. 638-648—American Chemical Society.
Corr Michael J. et al., "Amidine Dications as Superelectrophiles", Journal of the American Chemical Society, 2009, vol. 131(49), p. 17980-17985—American Chemical Society.
Rad-Moghadam Kurosh et al., "Indole 3-alkylation/vinylation under catalysis of the guanidinium ionic liquids", Tetrahedron, 2009, vol. 65(43), p. 8816-8820—Elsevier Ltd.

\* cited by examiner

*Primary Examiner* — Golam M Shameem

(57) ABSTRACT

A process for the preparation of the fluoroalkyl sulfonate salt of a nitrogen-based organic base said process comprising the step of reacting a fluoroalkyl sulfonyl halide with an organic base selected from the group consisting of tertiary amines, pyridines, amidines and guanidines.

16 Claims, No Drawings

PROCESS FOR THE SYNTHESIS OF FLUORALKYL SULFONATE SALTS

CROSS-REFERENCE TO RELATED APPLICATIONS

This application is a U.S. national stage entry under 35 U.S.C. § 371 of International Application No. PCT/EP2014/070952 filed Sep. 30, 2014, which claims priority to European application No. 13187325.9, filed on Oct. 4, 2013. The entire contents of these applications are explicitly incorporated herein by this reference.

TECHNICAL FIELD

The present invention relates to a process for the preparation of fluoroalkyl sulfonate salts of nitrogen-based organic bases.

BACKGROUND ART

Ionic liquids are liquids composed of ions that are liquid at temperatures of 100° C. or below. The very low vapour pressure, high thermal stability, and tuneable miscibility with other liquid phases that characterizes ionic liquids renders them interesting as alternatives to traditional organic liquids for several applications, including reaction media in synthesis, electrolytes in electrochemical processes or media in separation or analytical techniques.

Ionic liquids generally consist of an organic cation bearing alkyl substituents of variable chain length and an inorganic or organic anion. Among the most common cations, mention can be made of quaternary ammonium or phosphonium ions, N,N'-dialkylimidazolium, N-alkylpyridinium, N,N'-dialkylpyrrolidinium and guanidinium. Common anions are for instance $BF_4^-$, halogenides (Cl, Br, I), $PF_6^-$, carboxylates, alkylsulfonates, alkylsulfates, and thiocyanates.

Ionic liquids comprising a fluoroalkylsulfonate ion are known, see for instance US 20070100184 (DU PONT DE NEMOURS) May 3, 2007 and KULKARNI, P. S., et al. Comparison of physicochemical properties of new ionic liquids based on imidazolium, quaternary ammonium and guanidinium cations. *Chem. Eur. J.* 2007, vol. 13, p. 8478-8488.

Fluoroalkylsulfonate salts may also find use as surfactants.

Several processes have been described for the preparation of quaternary ammonium or guanidinium fluoroalkylsulfonate salts. In the references cited above the preparation involves an anion exchange, typically starting from the chloride of the quaternary ammonium or guanidinium cation.

More complex routes for the synthesis of the trifluoromethansulfonate salts have been described in KUNKEL, H., et al. Hexaalkylguanidinium trifluormethanesulfonate—A general synthesis from tetraalkylureas and triflic anhydride, and properties as ionic liquids. *Eur. J. Org. Chem.* 2007, p. 3476-3757., IGNAT'EV, N., et al. A convenient synthesis of triflate anionic liquids and their properties. *Molecules.* 2012, vol. 17, p. 5319-5338, and in US 20070265453 (MERK PATENT GMBH) Nov. 15, 2007.

None of these processes however disclose the preparation of fluoroalkylsulfonate salts of a wide array of nitrogen-based organic bases by a one pot reaction of a fluoroalkyl-sulfonyl halide with the nitrogen-based organic base.

BURDON, J., et al. Trifluoromethane sulfonate esters and their alkylating properties. *Tetrahedron.* 1965, vol. 21, p. 1-4, relates to the alkylating properties of trifluoromethanesulfonate esters. This document discloses the reaction of trifluoromethanesulphonyl fluoride with alcohols in the presence of pyridine; in particular, this document discloses the reaction of trifluoromethanesulphonyl fluoride with ethanol in the presence of pyridine to provide ethylpyridinium trifluoromethanesulfonate.

DE 1966931 (BAYER AG) May 28, 1975 discloses the synthesis of ammonium salts of general formula:

wherein:
—$R^1$-$R^4$ represent alkyl, alkenyl, cycloalkyl or alrylalkyl, or together with the N atom they are bound to, form a heterocyclic ring, and $R_f$ represents $C_1$-$C_{12}$ perfluorinated straight or branched alkyl. These salts are prepared by reaction of a tertiary amine, a perfluorinated sulfonyl fluoride and a silane ester. The reaction can be carried out in the presence of a polar inert solvent, like an ether, chloroform or acetonitrile.

U.S. Pat. No. 4,168,277 (BAYER AKTIENGESELL-SCHAFT) Sep. 18, 1979 discloses a process for the synthesis of a tetraethylammonium perfluoroalkyl sulfonate comprising reacting a perfluoroalkyl sulfonyl fluoride with triethylamine and an ethoxysilane in an inert solvent medium like chlorobenzene, ethers and toluene (col. 2, lines 53-54). The examples teach the use of chlorobenzene.

EP 0726249 A (HALDOR TOPSOE A/S) Aug. 14, 1996 discloses a process for base hydrolysis of a fluorinated sulfonyl fluoride with at least one mole equivalent of water and a tertiary amine to provide a salt of a corresponding fluorinated sulfonic acid with the amine.

EP 036094 A (MINESOTA MINING AN MANUFACTURING COMPANY) Apr. 11, 1990 discloses fluorochemical surfactants that are prepared by reacting at least one perfluoroalkyl sulfonyl fluoride having 3 to 20 carbon atoms, ethylene or propylene oxide, and at least one tertiary amine. It stems from the examples that the reaction occurs in the absence of solvents.

TAKAHASHI, K., et al. Development of triaryalmine mediator having ionic-tag and its application to electrocatalytic reaction in an ionic liquid. *Electrochimica Acta.* 2012, vol. 77, p. 47-53, discloses a process for the synthesis of:
 a trifluoromethanesulfonate salt of 4-[bis(4-bromophenyl) amino]benzyl triethylammonium and:
 a trifluoromethanesulfonate salt
  of 1-{4-[bis(4-bromophenyl)amino]benzyl}-3-methylimidazolium by reaction of of 4-[bis(4-bromophenyl) amino]benzyl alcohol, trifluoromethanesulfonyl chloride and triethylamine or 1-methyl imidazole in the presence of methylene chloride as the solvent.

SUMMARY OF INVENTION

Object of the present invention is a process for the preparation of a fluoroalkyl sulfonate salt of an organic base said process comprising the step of reacting a fluoroalkyl sulfonyl halide with an organic base selected from the group consisting of tertiary amines, pyridines, amidines, guanidines, imidazoles, piperidines and pirrolidines.

According to a preferred embodiment, the base is selected from tertiary amines, pyridines, amidines and guanidines.

According to another preferred embodiment, the base is selected from pyridines, amidines and guanidines.

According to a more preferred embodiment, the base is an amidine or a guanidine.

Any fluoroalkyl sulfonyl halide can be used in the process. The fluoroalkyl sulfonyl halide may be represented by formula (I):

$$R_fSO_2X \qquad (I)$$

wherein X is selected from F, Cl and Br. Preferably X is selected from F and Cl, more preferably X is F.

In formula (I), $R_f$ is selected from the group consisting of $C_1$ to $C_{25}$ straight-chain, branched or cyclic fluorinated alkane or alkene, optionally substituted and/or optionally comprising heteroatoms selected from the group consisting of O, N and S in the chain.

Preferably, $R_f$ is selected from the group consisting of $C_1$ to $C_{16}$ straight-chain, branched or cyclic fluorinated alkyl or alkenyl, optionally substituted and/or optionally comprising heteroatoms selected from the group consisting of O, N and S in the chain.

More preferably, $R_f$ is selected from the group consisting of $C_1$ to $C_{16}$ straight-chain, branched or cyclic fluorinated alkyl, optionally substituted and/or optionally comprising heteroatoms selected from the group consisting of O, N and S in the chain.

The expressions "fluoroalkyl" and "fluorinated" are used herein to refer to compounds that are either totally or partially fluorinated, i.e. wherein all or only a part of the hydrogen atoms have been replaced by fluorine atoms. Preferably, the expressions "fluoroalkyl" and "fluorinated" refer to compounds that contain a higher proportion of fluorine atoms than hydrogen atoms, more preferably the terms refer to compounds that are totally free of hydrogen atoms, i.e. wherein all the hydrogen atoms have been replaced by fluorine atoms. However, when the base is a tertiary amine or a pyridine, $R_f$ preferably contains at least one hydrogen atom.

Notable, non-limiting examples of group $R_f$ are —$CF_3$, —$CF_2CF_3$, —$CF_2CF_2H$, —$CF_2CFHCl$, —$C_3F_7$, —$CF_2CFHCF_3$, —$CF_2CFHOCF_3$, —$CF_2CF_2OCF_2CF_3$, —$CF_2CFHOCF_2CF_3$, —$CF_2CF_2OCFHCF_3$, —$CF_2CF_2OCF_2CF_2H$, —$CF_2CF_2OCF_2CF_2Cl$, —$CF_2CF_2OCFClCF_2Cl$, —$CF_2CFHOCF_2CF_2CF_3$, —$CF_2CF_2OCF_2CF_2OCF_2CF_2CF_3$, —$CF_2CF_2OCF(CF_3)OCF_2CF_3$. In one preferred embodiment, group $R_f$ is $CF_2CF_2OCFClCF_2Cl$.

Fluoroalkyl sulfonyl halides of formula $R_fSO_2X$ are known in the art and can be prepared according to established procedures.

The fluoroalkyl sulfonyl halide is reacted with an organic base selected from the group consisting of tertiary amines, pyridines, amidines, guanidines, imidazoles, piperidines and pirrolidines; preferably with an organic base selected from tertiary amines, pyridines, amidines and guanidines; more preferably with a base selected from pyridines, amidines and guanidines, even more preferably with a base selected from amidines and guanidines.

Tertiary amines suitable for the inventive process are selected among those of formula (II):

$$NR^1R^2R^3 \qquad (II)$$

wherein $R^1$, $R^2$ and $R^3$ are, independently of each other, selected from the group consisting of $C_1$ to $C_{25}$, preferably $C_2$ to $C_{20}$, straight-chain, branched or cyclic, optionally substituted, alkane or alkene, and $C_6$ to $C_{25}$, optionally substituted, aryl or heteroaryl.

Preferably in formula (II) $R^1$, $R^2$ and $R^3$, independently of each other, are selected from the group consisting of $C_1$ to $C_{10}$ straight-chain, branched or cyclic, alkanes.

Suitable pyridines may be selected among those of formula (III):

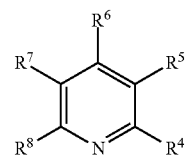

wherein each of $R^4$, $R^5$, $R^6$, $R^7$ and $R^8$, is independently selected from the group consisting of H, halogen, $C_1$ to $C_{25}$, preferably $C_1$ to $C_{20}$, straight-chain, branched or cyclic, optionally substituted, alkane or alkene, and $C_6$ to $C_{25}$, optionally substituted, aryl or heteroaryl. Preferably, each of $R^4$, $R^5$, $R^6$, $R^7$ and $R^8$, is independently selected from the group consisting of H, and $C_1$ to $C_{25}$, preferably $C_1$ to $C_{20}$, straight-chain, branched or cyclic, optionally substituted, alkane. Notable examples of suitable pyridines are for instance those complying with formula (III) wherein: $R^4$, $R^5$, $R^6$, $R^7$ and $R^8$ are all H; $R^4=R^8=CH_3$ and $R^5=R^6=R^7=H$; $R^4=R^6=R^8=CH_3$ and $R^5=R^7=H$; and $R^4=R^6=CH_3$ and $R^5=R^7=R^8=H$.

Suitable amidines for the process of the invention may be selected among the amidines of formula (IV):

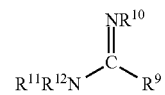

wherein $R^9$, $R^{10}$, $R^{11}$ and $R^{12}$, independently of each other, are selected from the group consisting of H, $C_1$ to $C_{25}$, preferably $C_1$ to $C_{20}$, straight-chain, branched or cyclic, optionally substituted, alkane or alkene, optionally containing heteroatoms; wherein up to four of $R^9$, $R^{10}$, $R^{11}$ and $R^{12}$ may be bonded to one another in pairs by single or double bond. Preferably, $R^9$, $R^{10}$, $R^{11}$ and $R^{12}$ are not all simultaneously H.

Up to all four substituents $R^9$, $R^{10}$, $R^{11}$ and $R^{12}$, may be bonded in pairs in such a way that mono-, bi- or poly-cyclic amidines are provided. In a preferred embodiment the amidine used in the process is a bicyclic amidine. Notable, non-limiting examples of such amidines are 1,8-diazabicyclo[5.4.0]undec-7-ene, 1,5-diazabicyclo[4.3.0]non-5-ene, 2,9-diazabicyclo[4.3.0]non-1,3,5,7-tetraene, and 6-(dibutylamino)-1,8-diazabicyclo[5.4.0]undecene-7.

Suitable guanidines for the process of the invention may be selected among the guanidines of formula (V):

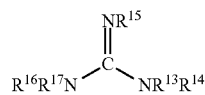

wherein $R^{13}$, $R^{14}$, $R^{15}$, $R^{16}$ and $R^{17}$ independently of each other, are selected from the group consisting of H, $C_1$ to $C_{25}$, preferably $C_1$ to $C_{20}$, straight-chain, branched or cyclic, optionally substituted, alkane or alkene, optionally containing heteroatoms; wherein up to four of $R^{13}$, $R^{14}$, $R^{15}$, $R^{16}$ and $R^{17}$ may be bonded to one another in pairs by single or double bond. Preferably, $R^{13}$, $R^{14}$, $R^{15}$, $R^{16}$ and $R^{17}$ are not simultaneously H. However it is preferred that at least one of $R^{13}$, $R^{14}$, $R^{15}$, $R^{16}$ and $R^{17}$ is H.

Notable, non-limiting examples of suitable guanidines are 1-methylguanidine, 1-ethylguanidine, 1-cyclohexylguanidine, 1-phenylguanidine, 1,1-dimethylguanidine, 1,3-dimethylguanidine, 1,2-diphenylguanidine, 1,1,2-trimethylguanidine, 1,2,3-tricyclohexylguanidine, 1,1,2,2-tetramethylguanidine, guanine, 1,5,7-triazabicyclo[4.4.0]-dec-5-ene, 7-methyl-1,5,7-triazabicyclo[4.4.0]dec-5-ene, 7-ethyl-1,5,7-triazabicyclo[4.4.0]dec-5-ene, 7-n-propyl-1,5, 7-triazabicyclo[4.4.0]dec-5-ene, 7-isopropyl-1,5,7-triazabicyclo[4.4.0]dec-5-ene, 7-n-butyl-1,5,7-triazabicyclo[4.4.0] dec-5-ene, 7-cyclohexyl-1,5,7-triazabicyclo[4.4.0]dec-5-ene, and 7-n-octyl-1,5,7-triazabicyclo[4.4.0]dec-5-ene.

The process is typically carried out in the liquid phase in the presence of a liquid reaction medium. The reaction medium is generally selected among aprotic polar organic solvents, optionally in the presence of water.

Suitable aprotic organic solvents for the process are for instance chlorinated solvents like dichloromethane; esters, like methylacetate, ethylacetate; ethers, like dioxane, tetrahydrofurane; nitriles, like acetonitrile.

The process is carried out at a temperature of from 0 to 100° C., generally from 15 to 80° C. In some instances it might be convenient to carry out the process at the boiling temperature of the organic solvent.

In a first embodiment of the process the fluoroalkyl sulfonyl halide of formula (I) is reacted with the organic base in the presence of an alcohol.

Any alcohol may be used in this first embodiment of the process. Suitable alcohols are typically selected from the group of $C_1$-$C_{20}$ straight-chain, branched or cyclic, optionally substituted, alkanols, $C_2$-$C_{20}$ straight-chain, branched or cyclic, optionally substituted, diols, $C_6$-$C_{20}$ aromatic or heteroaromatic, optionally substituted, alcohols.

Non limiting examples of suitable alcohols are for instance methanol, ethanol, n-butanol, benzyl alcohol.

This first embodiment of the process is particularly suitable for the preparation of fluoroalkyl sulfonate salts of organic bases selected from the group consisting of tertiary amines, pyridines and amidines.

According to this first embodiment of the process, if the alcohol is generically identified with formula R'OH, fluoroalkyl sulfonates of formulae (VI), (VII) and (VIII) are respectively obtained with the inventive process from amines of formula (II), pyridines of formula (III) and amidines of formula (IV), according to the following reaction schemes:

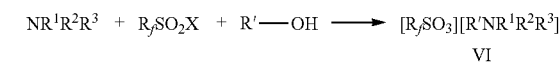

VI

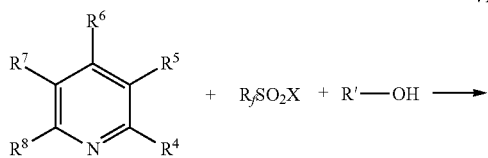

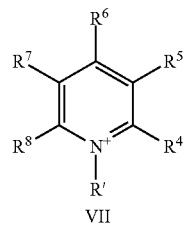

VII

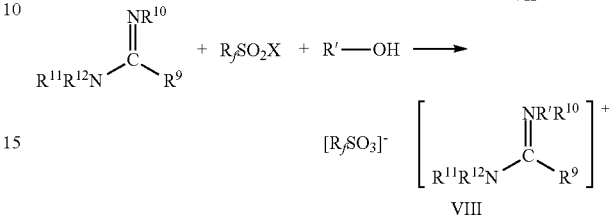

VIII wherein each one of $R_f$, $R^1$ to $R^{12}$ is as defined above and R' is selected from the group consisting of $C_1$-$C_{20}$ straight-chain, branched or cyclic, optionally substituted, alkyl optionally containing additional —OH groups, and $C_6$-$C_{20}$ optionally substituted aryl or heteroaryl.

Typically, the ratio of the fluoroalkyl sulfonyl halide to the organic base is at least 1:2, preferably from 1:2 to 1:3.

The alcohol is generally present in the reaction mixture at least in a 1:1 molar ratio with respect to the organic base.

In a second embodiment of the process, the fluoroalkyl sulfonyl halide of formula (I) is reacted with the organic base in the presence of water under basic conditions. The process according to this second embodiment has been found particularly suitable for the preparation of guanidinium fluoroalkyl sulfonates according to the following reaction scheme:

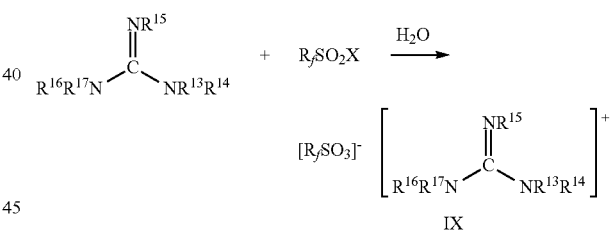

IX wherein in formula (IX) each one of $R_f$ and $R^{13}$ to $R^{17}$ are as defined above.

In the second embodiment of the process the ratio of the fluoroalkyl sulfonyl halide to the organic base is generally from 1:1 to 1:2, preferably about 1:1.

The reaction is carried out under basic conditions, that is at a pH greater than 7, typically of at least 8.

The fluoroalkyl sulfonate salts obtained according to any one of the embodiments of the inventive process may be recovered from the reaction mixture according to common separation and purification techniques.

A further embodiment of the invention is represented by fluoroalkyl sulfonate salts of an organic base selected from the group consisting of tertiary amines, pyridines, amidines, guanidines, imidazoles, piperidines and pirrolidines comprising a fluoroalkylsulfonyl group $R_f$ of formula $CF_2CF_2OCFClCF_2Cl$. Preferably, the salts are selected from formulae (VI)-(IX), preferably from formulae (VII)-(IX), more preferably from formulae (VIII) and (IX) as defined above, wherein $R_f$ is $CF_2CF_2OCFClCF_2Cl$. These salts are particularly useful in electrodeposition processes and in the manufacture of compositions for the electrodeposition of metals.

Should the disclosure of any patents, patent applications, and publications which are incorporated herein by reference conflict with the description of the present application to the extent that it may render a term unclear, the present description shall take precedence.

The invention will be now described in more detail with reference to the following examples whose purpose is merely illustrative and not limitative of the scope of the invention.

NMR spectra were recorded on a Varian Mercury 300 spectrometer operating at 282.180 MHz for $^{19}F$ and 299.316 MHz for $^1H$. $^{19}F$ NMR and $^1H$ NMR spectra of the compounds were recorded in DMSO and CDCl$_3$ at room temperature and the spectra were referenced to 1,3-hexafluoroxylene (HFMX −63.49 ppm) and TMS.

Transition temperatures (Melting and Glass transition temperature) were determined by DSC at a heating rate of 20° C./min following the procedure of ASTM D3418-08.

Weight loss determination was carried out using a TGA PYRIS 1 equipment from Perkin-Elmer according to method ASTM E 1131. A 10 mg sample of the polymer was subjected to constant heating in air at a rate of 10° C./min from 23° C. up to 750° C. The temperature, at which 1% weight loss is measured, is given.

EXAMPLES 1, 2, AND 3

Synthesis of methyl-triethyl ammonium (1), tetrabutyl ammonium (2) and dimethyl-dibenzyl ammonium (3) 2-(perfluoroethoxy)perfluorethanesulfonate To a three-necked round bottom flask equipped with thermometer and stirring were added CH$_2$Cl$_2$ (60 mL) and CF$_3$CF$_2$OCF$_2$CF$_2$SO$_2$F (10 g). The temperature of the mixture was brought to 0° C. Triethylamine (8.76 mL) was added and the mixture was allowed to stir at 0° C. for 30 minutes. Methanol (2.01 g) was added drop-wise. The temperature of the mixture was allowed to return to room temperature. After 2 hours the reaction was completed. The liquid phase was removed by evaporation under vacuum. The white solid was re-dissolved in CH$_2$Cl$_2$ (50 mL) and extracted with an aqueous NaOH solution (70 mL). The organic phase was separated from the aqueous phase. The aqueous phase was treated with Na$_2$SO$_4$ and the product recovered by evaporation under vacuum. Methyl-triethyl ammonium 2-(perfluoroethoxy)perfluorethanesulfonate (Example 1, 11.7 g) was isolated as a white solid in 87% yield (melting point 154° C.; 1% weight loss: 312° C.).

$^{19}F$ NMR (HFMX reference): −84.1 ppm (m; 2F; —OCF$_2$CF$_2$—); −88.2 ppm (s; 3F; —CF$_3$); −90.1 ppm (m; 2F; CF$_3$CF$_2$O—); −120.1 ppm (s; 2F; —CF$_2$SO$_3^−$). $^1H$ NMR (TMS reference): +3.26 ppm (q; 6H; —NCH$_2$CH$_3$); +2.88 ppm (s; 3H; CH$_3$—N—); +1.22 ppm (m; 9H; —NCH$_2$CH$_3$).

Following a similar procedure, tetrabutyl ammonium 2-(perfluoroethoxy)perfluorethanesulfonate (Example 2, melting point −45.7° C.; 1% weight loss: 291° C.) was obtained in 59% yield from CF$_3$CF$_2$OCF$_2$CF$_2$SO$_2$F (30 g), n-butanol (13.98 g) and tri(n-butyl)amine (34.97 g).

$^{19}F$ NMR (HFMX reference): −84.1 ppm (m; 2F; —OCF$_2$CF$_2$—); −88.2 ppm (s; 3F; —CF$_3$); −90.1 ppm (m; 2F; CF$_3$CF$_2$O—); −120.1 ppm (s; 2F; —CF$_2$SO$_3^−$). $^1H$ NMR (TMS reference): +3.14 ppm (m; 8H; NCH$_2$—); +1.55 ppm (m; 8H; NCH$_2$CH$_2$—); +1.28 ppm (m; 8H; —CH$_2$CH$_3$); +0.90 ppm (t; 12H; —CH$_2$CH$_3$).

Dimethyl-dibenzyl ammonium 2-(perfluoroethoxy)perfluorethanesulfonate (Example 3, melting point 62.3° C.; 1% weight loss: 289° C.) was obtained in 85% yield from CF$_3$CF$_2$OCF$_2$CF$_2$SO$_2$F (25 g), benzyl alcohol (17.00 g) and dimethyl-benzyl amine (21.26 g) was obtained according to a similar procedure, the isolation of the product further comprising treatment with n-hexane for separation of the unreacted alcohol and amine.

$^{19}F$ NMR (HFMX reference): −84.1 ppm (m; 2F; —OCF$_2$CF$_2$—); −88.2 ppm (s; 3F; —CF$_3$); −90.1 ppm (m; 2F; CF$_3$CF$_2$O—); −120.1 ppm (s; 2F; —CF$_2$SO$_3^−$). $^1H$ NMR (TMS reference): +7.55 ppm (m; 10H; Ph-); +4.58 ppm (s; 4H; —NC H$_2$Ph); +2.84 ppm (s; 6H; —NCH$_3$).

EXAMPLE 4

Synthesis of N-methyl-2,4,6-trimethyl-pyridinium 2-(perfluoroethoxy)perfluorethanesulfonate Following a procedure similar to the one described for Example 1, CF$_3$CF$_2$OCF$_2$CF$_2$SO$_2$F (20 g) was reacted with 2,4,6-trimethylpyridine (15.24 g) in the presence of methanol (4.03 g) in CH$_2$Cl$_2$ (80 mL) at room temperature. N-methyl-2,4,6-trimethyl-pyridinium 2-(perfluoroethoxy)perfluorethanesulfonate (melting point 83.2° C., 1% weight loss: 323° C.) was isolated as a white solid in 87% yield.

$^{19}F$ NMR (HFMX reference): −84.1 ppm (m; 2F; —OCF$_2$CF$_2$—); −88.2 ppm (s; 3F; —CF$_3$); −90.1 ppm (m; 2F; CF$_3$CF$_2$O—); −120.1 ppm (s; 2F; —CF$_2$SO$_3^−$). $^1H$ NMR (TMS reference): +7.70 ppm (s; 2H; meta-H); +3.96 ppm (s; 3H; NCH$_3$); +2.72 ppm (s; 6H; ortho-CH$_3$); +2.47 ppm (s; 3H; para-CH$_3$).

EXAMPLE 5

Synthesis of N-methyl-1,8-diazabicyclo[5.4.0]undec-7-enium 2-(perfluoroethoxy)perfluorethanesulfonate Following a procedure similar to the one described for Example 1, CF$_3$CF$_2$OCF$_2$CF$_2$SO$_2$F (27 g) was reacted with 1,8-diazabicyclo[5.4.0]undec-7-ene (16.80 g) in the presence of methanol (5.44 g) in CH$_2$Cl$_2$ at room temperature. A mixture of N-methyl-1,8-diazabicyclo[5.4.0]undec-7-enium 2-(perfluoroethoxy)perfluorethanesulfonate and 1,8-diazabicyclo[5.4.0]undec-7-enium 2-(perfluoroethoxy)perfluorethanesulfonate (melting point of the mixture −60° C.) was isolated as a yellow oil in 72.8% yield.

EXAMPLES 6 AND 7

Synthesis of 1,5,7-triazabicyclo[4.4.0]-dec-5-enium 2-(1,2-dichloro-1,1,2-trifluoroethoxy)perfluorethanesulfonate (6) and of N,N,N',N'-tetramethylguanidinium 2-(1,2-dichloro-1,1,2-trifluoroethoxy)perfluorethanesulfonate (7)

To a three-necked round bottom flask equipped with thermometer and stirring containing CH$_2$Cl$_2$ (305 g) and 1,5,7-triazabicyclo[4.4.0]-dec-5-ene (55.55 g) was added a solution of K$_2$CO$_3$ in water (4 M) followed by CF$_2$ClCFClOCF$_2$CF$_2$SO$_2$F (140.05 g), added drop-wise. The temperature of the mixture was kept to room temperature. After 2 hours the reaction was completed. A biphasic system was obtained. The organic phase was separated from the aqueous one, washed with water, treated with MgSO$_4$ and any solid filtered off. The product was recovered by evaporation under vacuum in 84% yield (melting point 67° C.; 1% weight loss: 304° C.).

$^{19}$F NMR (HFMX reference): −70.9 ppm (d; 2F; ClCF$_2$—); −76.5 ppm (m; 1F; —CFClO—); −83.3 ppm (m; 2F; —OCF$_2$CF$_2$—); −118.5 ppm (s; 2F; —CF$_2$SO$_3^-$). $^1$H NMR (TMS reference): +3.30 ppm (m; 8H; —NCH$_2$—); +2.00 ppm (m; 4H; —CH$_2$—).

Following a similar procedure, N,N,N',N'-tetramethylguanidinium 2-(perfluoroethoxy)perfluorethanesulfonate (Example 7, melting point 71° C.; TGA 259° C.) was obtained in 98% yield from CF$_2$ClCFClOCF$_2$CF$_2$SO$_2$F (121.90 g) and N,N,N',N'-tetramethylguanidine (40.00 g).

$^{19}$F NMR (HFMX reference): −70.9 ppm (d; 2F; ClCF$_2$—); −76.5 ppm (m; 1F; —CFClO—); −83.3 ppm (m; 2F; —OCF$_2$CF$_2$—); −118.5 ppm (s; 2F; —CF$_2$SO$_3^-$). $^1$H NMR (TMS reference): +2.95 ppm (s; 12H; CH$_3$N—).

The inventive process thus provides a simple and convenient one-pot synthesis of fluoroalkyl sulfonate salts of nitrogen containing organic bases in high yields and purity.

The invention claimed is:

1. A process for the preparation of a fluoroalkyl sulfonate salt of any one of formula (VII), formula (VIII) or formula (IX):

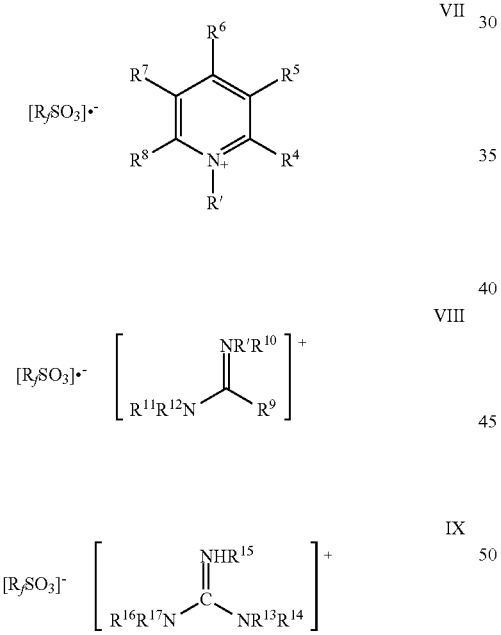

wherein:
R$_f$ is selected from the group consisting of C$_1$ to C$_{25}$ straight-chain, branched or cyclic fluorinated alkyl or alkenyl, optionally substituted and/or optionally comprising heteroatoms selected from the group consisting of O, N and S in the chain;
each of R$^4$, R$^5$, R$^6$, R$^7$ and R$^8$, is independently selected from the group consisting of H, halogen, C$_1$ to C$_{25}$ straight-chain, branched or cyclic, optionally substituted, alkane or alkene, and C$_6$ to C$_{25}$, optionally substituted, aryl or heteroaryl;
each of R$^9$, R$^{10}$, R$^{11}$ and R$^{12}$, is independently selected from group consisting of H, C$_1$ to C$_{25}$ straight-chain, branched or cyclic, optionally substituted, alkane or alkene, optionally containing heteroatoms, wherein up to four of R$^9$, R$^{10}$, R$^{11}$ and R$^{12}$ may be bonded to one another in pairs by single or double bond; and
each of R$^{13}$, R$^{14}$, R$^{15}$, R$^{16}$ and R$^{17}$, is independently selected from the group consisting of H, C$_1$ to C$_{25}$ straight-chain, branched or cyclic, optionally substituted, alkane or alkene, optionally containing heteroatoms, wherein up to four of R$^{13}$, R$^{14}$, R$^{15}$, R$^{16}$ and R$^{17}$ may be bonded to one another in pairs by single or double bond;

said process comprising the step of reacting a fluoroalkyl sulfonyl halide with an organic base selected from the group consisting of:

pyridines of formula (III):

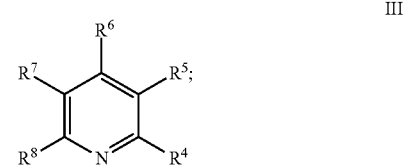

amidines of formula (IV):

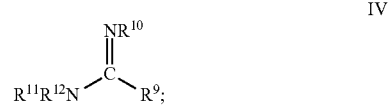

and
guanidines of formula (V):

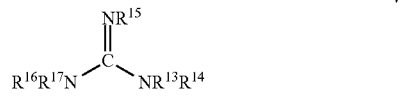

wherein R$^4$-R$^{17}$ are as defined above,
in the presence of an alcohol when using a pyridine or amidine organic base; or in the presence of water under basic conditions when using a guanidine organic base.

2. The process of claim 1 wherein the fluoroalkyl sulfonyl halide is selected from the group consisting of the fluoroalkyl sulfonates of formula (I) R$_f$SO$_2$X, wherein X is selected from F, Cl and Br; and R$_f$ is selected from the group consisting of C$_1$ to C$_{25}$ straight-chain, branched or cyclic fluorinated alkyl or alkenyl, optionally substituted and/or optionally comprising heteroatoms selected from the group consisting of O, N and S in the chain.

3. The process of claim 1, wherein the fluoroalkyl sulfonyl halide is reacted with the organic base in the presence of an alcohol.

4. The process of claim 3 wherein the organic base is selected from the group consisting of pyridines and amidines.

5. The process of claim 3, wherein fluroalkyl sulfonates of formulae (VII) and (VIII) are prepared by reacting a fluoro alkyl sulfonate of formula (I) with pyridines of formula (III) and amidines of formula (IV), and an alcohol of formula R'OH:

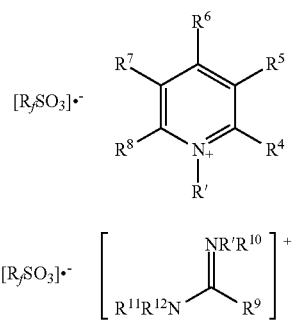

wherein $R_f$ is selected from the group consisting of $C_1$ to $C_{25}$ straight-chain, branched or cyclic fluorinated alkyl or alkenyl, optionally substituted and/or optionally comprising heteroatoms selected from the group consisting of O, N and S in the chain; each of $R^4$, $R^5$, $R^6$, $R^7$ and $R^8$, is independently selected from the group consisting of H, halogen, $C_1$ to $C_{25}$ straight-chain, branched or cyclic, optionally substituted, alkane or alkene, and $C_6$ to $C_{25}$, optionally substituted, aryl or heteroaryl; each of $R^9$, $R^{10}$, $R^{11}$ and $R^{12}$, is independently selected from group consisting of H, $C_1$ to $C_{25}$ straight-chain, branched or cyclic, optionally substituted, alkane or alkene, optionally containing heteroatoms, wherein up to four of $R^9$, $R^{10}$, $R^{11}$ and $R^{12}$ may be bonded to one another in pairs by single or double bond; and R' is selected from the group consisting of $C_1$-$C_{20}$ straight-chain, branched or cyclic, optionally substituted, alkyl optionally containing additional —OH groups, and $C_6$-$C_{20}$ optionally substituted aryl or heteroaryl.

6. The process of claim 1, wherein the fluoroalkyl sulfonyl halide is reacted with the organic base in the presence of water under basic conditions.

7. The process of claim 6, wherein the organic base is a guanidine.

8. The process of claim 7, wherein a guanidinium fluoro alkyl sulfonate of formula (IX) is obtained:

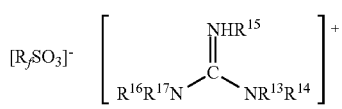

wherein $R_f$ is selected from the group consisting of $C_1$ to $C_{25}$ straight-chain, branched or cyclic fluorinated alkyl or alkenyl, optionally substituted and/or optionally comprising heteroatoms selected from the group consisting of O, N and S in the chain; and each of $R^{13}$, $R^{14}$, $R^{15}$, $R^{16}$ and $R^{17}$, is independently selected from the group consisting of H, $C_1$ to $C_{25}$ straight-chain, branched or cyclic, optionally substituted, alkane or alkene, optionally containing heteroatoms, wherein up to four of $R^{13}$, $R^{14}$, $R^{15}$, $R^{16}$ and $R^{17}$ may be bonded to one another in pairs by single or double bond.

9. The process of claim 1, wherein $R_f$ is selected from the group consisting of $C_1$ to $C_{16}$ straight-chain, branched or cyclic fluorinated alkyl, optionally substituted and/or optionally comprising heteroatoms selected from the group consisting of O, N and S in the chain.

10. The process of claim 1, wherein $R_f$ is selected from —$CF_3$, —$CF_2CF_3$, —$CF_2CF_2H$, —$CF_2CFHCl$, —$C_3F_7$, —$CF_2CFHCF_3$, —$CF_2CFHOCF_3$, —$CF_2CF_2OCF_2CF_3$, —$CF_2CFHOCF_2CF_3$, —$CF_2CF_2OCFHCF_3$, —$CF_2CF_2OCF_2CF_2H$, —$CF_2CF_2OCF_2CF_2Cl$, —$CF_2CF_2OCFClCF_2Cl$, —$CF_2CFHOCF_2CF_2CF_3$, —$CF_2CF_2OCF_2OCF_2CF_2CF_3$, —$CF_2CF_2OCF(CF_3)OCF_2CF_3$.

11. The process of claim 1, wherein $R_f$ is $CF_2CF_2OCFClCF_2Cl$.

12. The process of claim 1, wherein the organic base is a pyridine of formula (III) and wherein:
$R_4$, $R_5$, $R_6$, $R_7$ and $R_8$ are all H; or
$R_4$ and $R_8$ are $CH_3$ and $R_5$, $R_6$, $R_7$ are H; or
$R_4$, $R_6$ and $R_8$ are $CH_3$ and $R_5$ and $R_7$ are H; or
$R_4$ and $R_6$ are $CH_3$ and $R_5$, $R_7$ and $R_8$ are H.

13. The process of claim 1, wherein the organic base is an amidine selected from 1,8-diazabicyclo[5.4.0]undec-7-ene, 1,5-diazabicyclo[4.3.0]non-5-ene, 2,9-diazabicyclo[4.3.0]non-1,3,5,7-tetraene, and 6-(dibutylamino)-1,8-diazabicyclo[5.4.0]undecene-7.

14. The process of claim 1, wherein the organic base is a guanidine selected from 1-methylguanidine, 1-ethylguanidine, 1-cyclohexylguanidine, 1-phenylguanidine, 1,1-dimethylguanidine, 1,3-dimethylguanidine, 1,2-diphenylguanidine, 1,1,2-trimethylguanidine, 1,2,3-tricyclohexylguanidine, 1,1,2,2-tetramethylguanidine, guanine, 1,5,7-triazabicyclo[4.4.0]-dec-5-ene, 7-methyl-1,5,7-triazabicyclo[4.4.0]dec-5-ene, 7-ethyl-1,5,7-triazabicyclo[4.4.0]dec-5-ene, 7-n-propyl-1,5,7-triazabicyclo[4.4.0]dec-5-ene, 7-isopropyl-1,5,7-triazabicyclo[4.4.0]dec-5-ene, 7-n-butyl-1,5,7-triazabicyclo[4.4.0]dec-5-ene, 7-cyclohexyl-1,5,7-triazabicyclo[4.4.0]dec-5-ene, and 7-n-octyl-1,5,7-triazabicyclo[4.4.0]dec-5-ene.

15. The process of claim 4, wherein the ratio of the fluoroalkyl sulfonyl halide to organic base is at least 1:2.

16. The process of claim 7, wherein the ratio of the fluoroalkyl sulfonyl halide to organic base is from 1:1 to 1:2.

* * * * *